(12) United States Patent
Wilks et al.

(10) Patent No.: US 6,218,516 B1
(45) Date of Patent: Apr. 17, 2001

(54) ANTIBODIES SPECIFIC FOR THE EXTRACELLULAR DOMAIN OF NYK/FLK-1 PROTEIN AND USES THEREOF

(75) Inventors: Andrew F Wilks, Doncaster East; Steven A Stacker, North Fitzroy; Robert B Oelrichs, Northcote, all of (AU)

(73) Assignee: Ludwig Institute for Cancer Research, London (GB)

( * ) Notice: Subject to any disclaimer, the term of this patent is extended or adjusted under 35 U.S.C. 154(b) by 0 days.

(21) Appl. No.: 08/693,211

(22) PCT Filed: Feb. 9, 1995

(86) PCT No.: PCT/US95/01727

§ 371 Date: Sep. 30, 1996

§ 102(e) Date: Sep. 30, 1996

(87) PCT Pub. No.: WO95/21865

PCT Pub. Date: Aug. 17, 1995

(30) Foreign Application Priority Data

Feb. 10, 1994 (AU) .................................................. PM3793

(51) Int. Cl.[7] ........................ C07K 16/00; G01N 33/53; A61K 39/395
(52) U.S. Cl. .................. 530/388.24; 435/7.2; 424/145.1
(58) Field of Search ........................... 530/387.1, 388.24; 424/130.1, 145.1; 435/7.1, 7.2, 7.9

(56) References Cited

U.S. PATENT DOCUMENTS 5,747,651   5/1998   Lemischka ........................ 530/387.9

OTHER PUBLICATIONS

Millauer et al. Cell 72:835–46 (1993).
Matthews et al. Proc. Natl. Acad. Sci. 88:9026–30 (1991).
Oelrichs et al. Oncogene 8:11–18 (1993).
Harlow & Lane (1988) Cold Spr. Harbor Lab. Press. Chapters 5, 6, & 9.

*Primary Examiner*—Sheela Huff
*Assistant Examiner*—Yvonne Eyler
(74) *Attorney, Agent, or Firm*—Fulbright & Jaworski, LLP

(57) ABSTRACT

The present invention relates to immunointeractive molecules and their use in therapeutics and diagnostics. More particularly, the present invention provides antibodies that bind to NYK/flk-1 receptors, in particular the extracellular domain.

7 Claims, 5 Drawing Sheets

FIG. 1

Asp-Tyr-Lys-Asp-Asp-Asp-Lys-STOP  [SEQ ID NO:1]

5'gatctgactacaaggacgacgatgacaagtgaatcgata 3' [SEQ ID NO:2]
3'actgatgttcctgctgctactgttcacttagctatctag 5' [SEQ ID NO:3]

BglII        ClaI        BglII

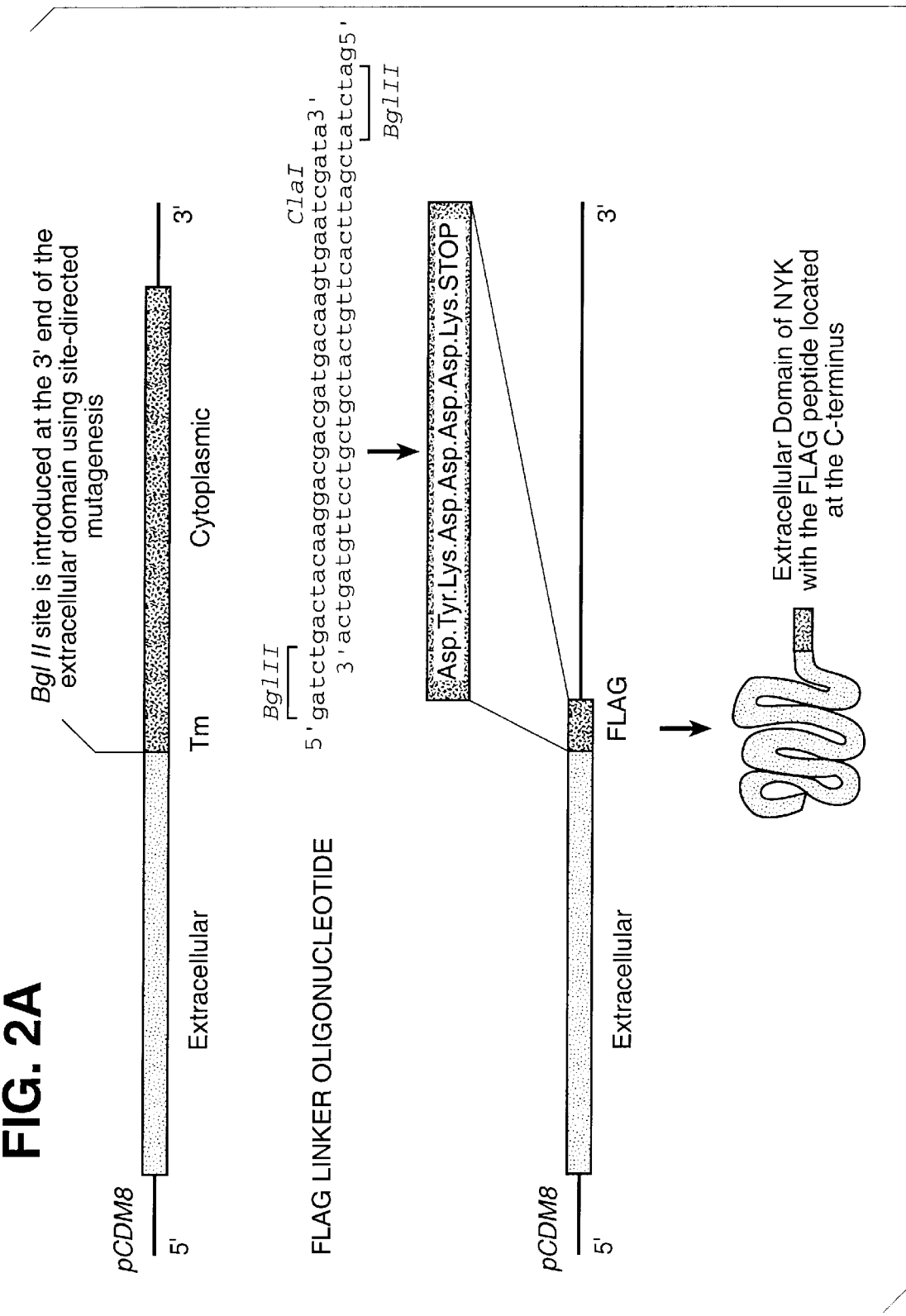

D1-D7AP

D1-D5AP

D1-D2D3AP

D1-D2AP

ANTIBODIES SPECIFIC FOR THE EXTRACELLULAR DOMAIN OF NYK/FLK-1 PROTEIN AND USES THEREOF

FIELD OF THE INVENTION

The present invention relates to immunointeractive molecules to an animal growth factor receptor and, more particularly, to animal neuroepithelial kinase/fetal liver kinase-1 receptor (NYK/flk-1). The immunointeractive molecules provide the basis for new therapeutic and diagnostic agents which can be used, for example, in the treatment, prophylaxis and diagnosis of an angiogenic-dependent phenotype.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND OF THE INVENTION

Angiogenesis is the formation of new blood vessels from those which preexist within the body (1). It is of fundamental importance for the development of the embryo and a number of roles in post-natal life (e.g. wound healing, tissue regeneration, cyclical growth of the corpus luteum and endometrium). Angiogenesis is also important in a number of pathological conditions including the growth of solid tumors (1). Recent studies have suggested that the acquistion of an angiogenic-dependent phenotype is a key factor in the development of metastasis.

The introduction of techniques based on the polymerase chain reaction (PCR) for amplifying protein tyrosien kinase sequences has enabled the rapid isolation of novel members of the growth factor receptor family. Two of the putative receptors isolated NYK/flk-1 (2) (neuroepithelial kinase/fetal liver kinase) and tie2/Tek (3) have been shown to be expressed on endothelial cells and their precursors. NYK and its human equivalent KDR (4) have been shown to bind and be activated by the endothelial cell mitogen VEGF/VPF (vascular endothelial growth factor/vascular premeability factor) (5). VEGF has a mitagenic effect on endothelial cells but is also a potent mediator of vascular permeability. VEGF has in recent studies been shown to play a role in the hypoxia induced angiogenesis seen in a glioma model suggesting the VEGF may play a role in meadiating angiogenesis in other tumour systems (6). Other studies have shown that anti-VEGF monoclonal antibodies have an anti-tumour effect in vivo (7).

In work leading up to the present inventions the inventors developed a series of antibodies to the NYK (VEGF2R) receptor extracellular domain. These antibodies are useful in the development of a new range of therapeutic molecules such as agonists and antagonists of the NYK-VEGF interaction as well as a range of diagnostic agents capable of, for example, detecting normal or mutated NYK receptors, receptor expression on a cell surface and/or receptor-ligand interaction.

SUMMARY OF THE INVENTION

One aspect of the present invention provides an immunointeractive molecules capable of binding or otherwise associated with an animal NYK/flk-1 receptor extracellular domain. Preferably, the animal is a mammal such as a human or murine animals. Preferably, the immunointeractive molecule is a polyclonal or monoclonal antibody.

Another aspect of the present invention is directed to a diagnostic agent comprising an immunointeractive molecule capable of binding or otherwise associating with an animal NYK/flk-1 receptor extracellular domain. Preferably, the immunointeractive molecule is an antibody labelled with a reporter molecule.

Yet another aspect of the present invention relates to a pharmaceutical composition comprising an immunointeractive molecule as contemplated above together with one or more pharmaceutically acceptable carriers and/or diluents.

Still another aspect of the present invention provides a method for treating an angiogenic-dependent phenotype or disease condition resulting therefrom in a mammal, said method comprising administering to said mammal an effective amount of an immunointeractive molecule capable of binding or otherwise associating with an animal NYK/flk-1 receptor extracellular domain. The method is particulary useful in the treatment of metastasis.

A further aspect of the present invention is the use of the subject interactive molecules to treat metastases by targeting isotypes such as $^{125}$I and $^{131}$I.

Figure 2B:
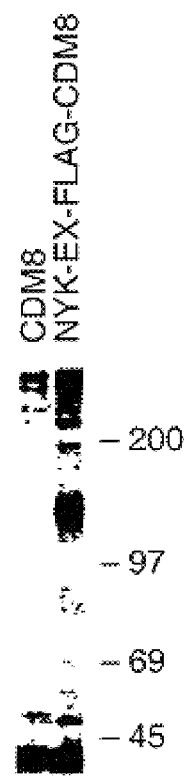
FIG. 2(A) is a schematic representation showing that an in frame BgIII site was introduced into the NYK cDNA clone at the extracellular/transmembrane junction using site directed mutagenesis. The FLAG™ linker oligonucleotides were ligated into BgIII site and ligated plasmids selected by restriction enzyme digest with ClaI. (B) The selected clones were then transiently transfected into COS cells and shown to produce a protein of the predicted size for NYK-EX-FLAG™.
Figure 3:
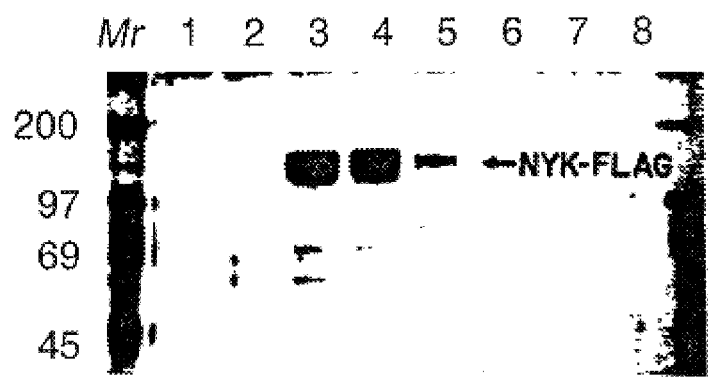
FIG. 3 is a photographic representation showing that NYK-EX-FLAG™ was purified from the conditioned medium of CHO cells stably transfected with the pEE6-NYK-EX-FLAG™ construct by affinity chromatography on M2-gel. NYK-EX-FLAG™ was eluted with 30 μg/ml of free FLAG™ peptide in 10 mM Tris-HCl pH 8.0, 150 mM NaCl, 0.02% v/v Tween 20. Fractions (10 μl of 1000) were analysed by SDS-PAGE and silver staining. Molecular weight markers are indicated and are 200, 97, 69 and 45 kDa.
Figure 4A:
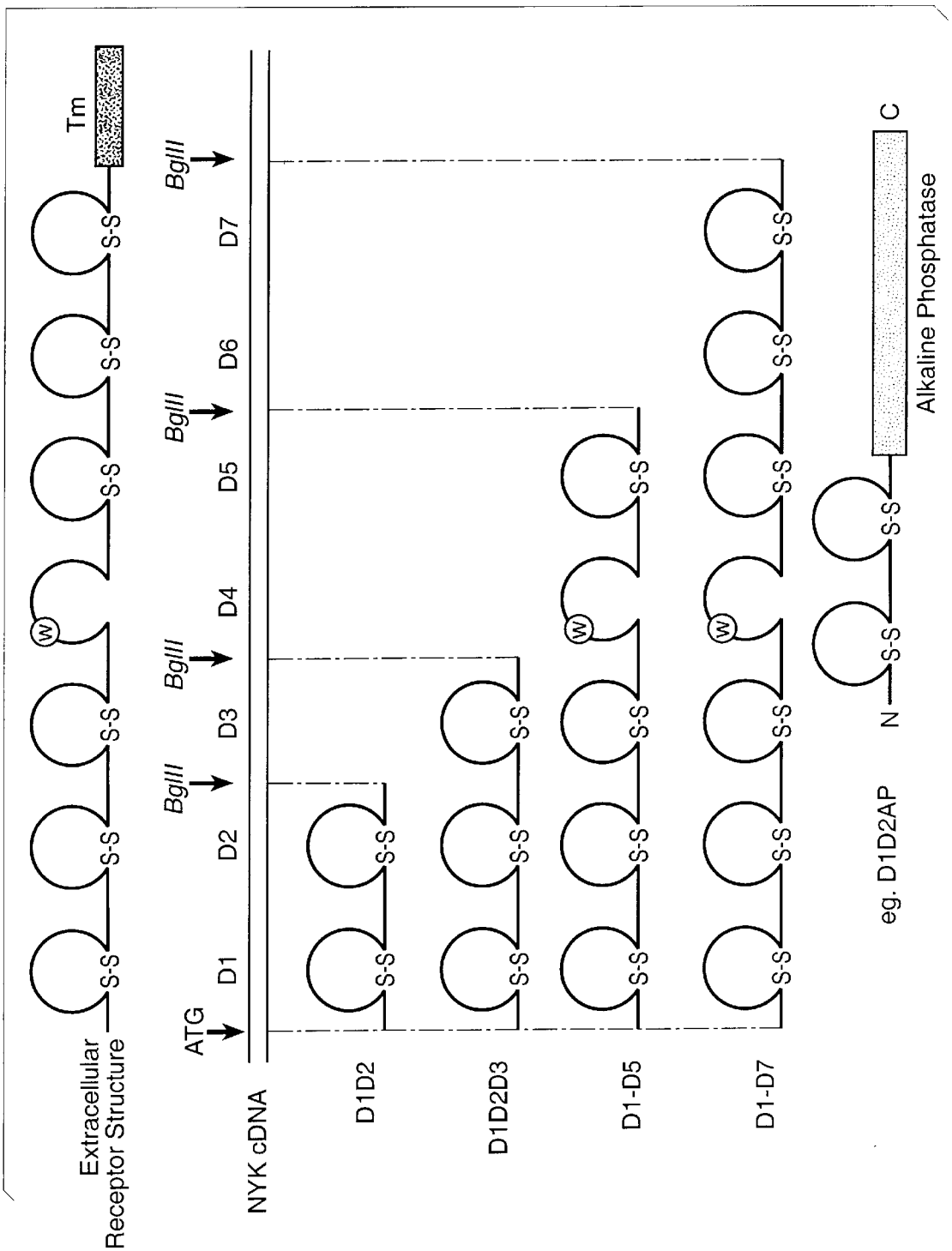
FIG. 4A is a schematic representation of the soluble mutant forms of the NYK receptor extracellular domain. Using site directed mutagenesis in frame BgIII sites were introduced at select sites within the receptor cDNA sequence to produce mutants which encode truncated versions of the NYK receptor. These mutants were then ligated into the expression vector AP-TAG-1 to produce fusion proteins which had Ig-like domains of NYK ligated to secreted alkaline phosphatase. The mutant forms are D1-D2-AP (domains 1 and 2 coupled to alkaline phosphatase), D1-D2-D3-AP, D1-D5-AP and D1-D7-AP.
Figures 1, 4B:
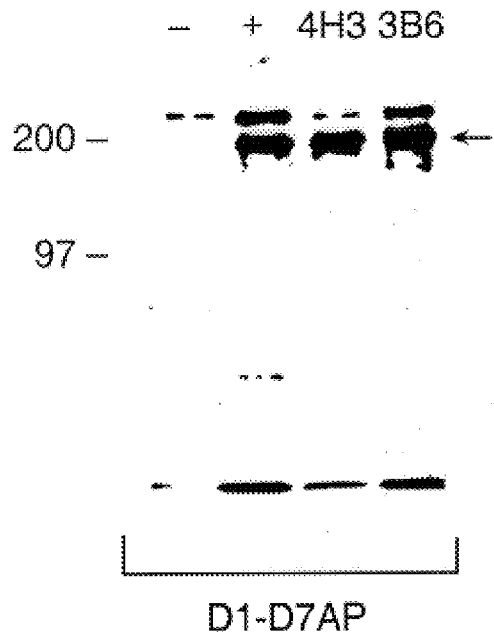
FIG. 1 is a representation of the FLAG™ linker oligonucleotides which encode the sequence of the FLAG™ marker peptide with BgIII compatible ends for ligation into the mutant NYK receptor cDNA containing the BgIII site at the predicted extracellular/transmembrane junction.
FIG. 4B is a photographic representation showing immunoprecipitation of the NYK receptor domain mutants. NIH-3T3 cells transfected with the D1-D2, D1-D2-D3, D1-D5 and D1-D7 domain constructs subcloned into the AP-TAG-1 vector were biosynthetically labelled for 16 hours with $^{35}$S-Cys/Met. Supernatants from these cells were immunoprecipitated with either 10 μl of Rabbit Ig-Sepharose, anti-AP-Sepharose, 4H3-Sepharose or 3B6-Sepharose beads.
Figures 2, 4B:
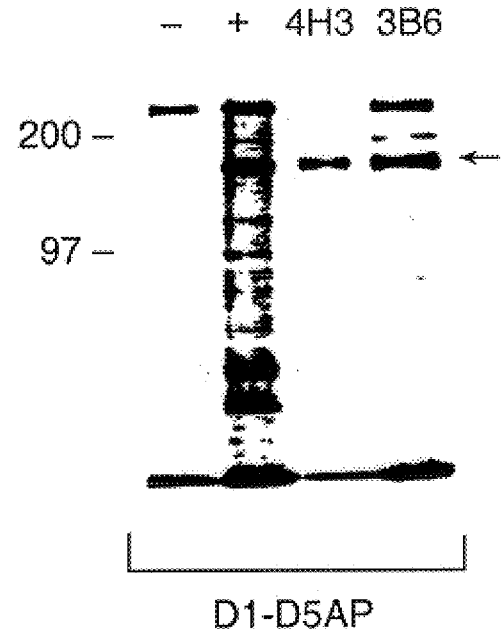
Figures 3, 4B:
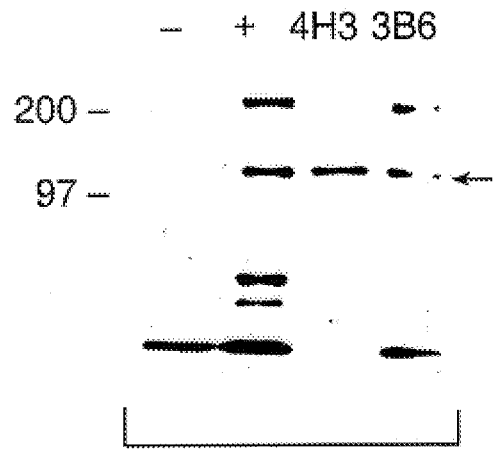
Figures 4, 4B:
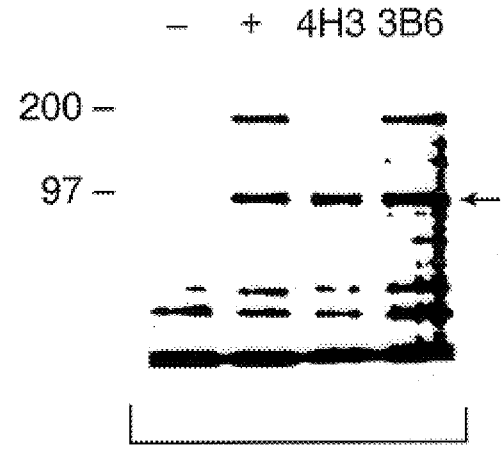

After 2 hours at 4° C. the immunoprecipitates were washed and eluted with SDS-PAGE sample buffer and boiling for 5 mins. Samples were analysed by SDS-PAGE, the gels dried and exposed to a phosphoimager cassette. Molecular weight markers are indicated. The predicted size of the fusion proteins including use of potential glycosylation sites are D1-D2-AP 103,000; D1-D2-D3-AP 122,000; D1-D5-AP 158,000 and D1-D7-AP 191,000.

DETAILED DESCRIPTION OF THE PREFERRED EMBODIMENTS

One aspect of the present invention provides an immunointeractive molecule capable of binding or otherwise associating with an animal NYK/flk-1 receptor, and in particular, the extracellular domain of such a receptor.

Preferably, the immunointeractive molecules are in the form of antibodies such as polyclonal or monoclonal antibodies although monoclonal antibodies are preferred. The present invention also extends to immunologically interactive fragments, parts, derivatives, homologues or analogues of these antibodies. Such antibodies may be in isolated or purified form meaning that a composition comprises at least 25%, more preferably at least 35%, even more preferably at least 45–50%, still more preferably at least 60–75% and even still more preferably at least 80–95% of the antibodies as determined by weight, immunoreactivity or other convenient means. Alternatively, the antibodies may be present in the form of isolated culture supernatant, tissue extract, serum of whole blood or ascites fluid.

Preferably, the animal NYK/flk-1 receptor is a mammalian origin such as from a human, livestock animal (e.g. cow, horse, sheep, goat or donkey), laboratory test animal (e.g. rat, mouse or rabbit), companion animal (e.g. dog or cat) or captive wild animal (e.g. dingo, fox, wild boar or kangaroo). The most preferred receptors are of human and laboratory test animal origin (e.g. rat or mouse).

Where the antibodies are polyclonal antibodies, they may be generated in any convenient host including a human, livestock animal, companion animal or captive wild animal as exemplified. Where the antibodies are monoclonal antibodies, they may be prepared in any convenient hybridoma such as a murine (e.g. rat or mouse) origin.

The receptor used to generate the antibodies may be the whole receptor such as in purified, partially purified or isolated form including in the form of isolated membrane preparations. The receptor may also be produced by recombinant procedures or synthetic procedures or a combination thereof. In a particularly preferred embodiment, a fragment of the receptor is used which, in an even more preferred embodiment, is fused to a suitable carrier or marker molecule such as FLAG™ protein. An example of another carrier is alkaline phosphatase (AP). Glutathione-S-transferase (GST) may also be used, although it may first require modification to facilitate induction of monoclonal antibodies.

According to this preferred embodiment, there is provided a molecule interactive with a non-full length NYK/flk-1 receptor fused to a carrier molecule. Preferably, the non-full length receptor comprises its extracellular domain. Preferably, the carrier molecule is FLAG™ or AP.

The resulting fusion molecule is then used to generate polyclonal or monoclonal antibodies which may undergo immunoadsorbent procedures to provide a composition of substantially, for example, extracellular domain-reactive receptor antibodies.

The term "immunointeractive molecules" is used herein in its broadcast sense and includes antibodies, parts, fragments, derivatives, homologues or analogues thereof, peptide or non-peptide equivalents thereof and fusion molecules between two or more antibodies or between an antibody and another molecule. The antibodies or other immunointeractive molecules may also be in recombinant or synthetic form. Where the interactive molecules are antibodies, these may be generated in a number of different species such as humans, mice and rats.

Accordingly, the present invention contemplates mutants and derivatives of the immunointeractive molecules, especially when such molecules are antibodies. Mutants and derivatives of such antibodies include amino acid substitutions, deletions and/or additions. Furthermore, amino acids may be replaced by other amino acids having like properties, such as hydrophobicity, hydrophilicity, electronegativity, bulky side chains, interactive and/or functional groups and so on. Glycosylation variants and hybrid antibodies are also contemplated by the present invention.

Amino acid substitutions are typically of single residues; insertions will usually be of the order of about 1–10 amino acid residues; and deletions will range from about 1–20 residues. Deletions or insertions preferably are made in adjacent pairs, i.e.: a deletion of 2 residues or insertion of 2 residues.

The amino acid variants referred to above may readily be made using snythetic peptide techniques well known in the art, such as solid phase peptide synthesis and the like, or by recombinant DNA manipulations. Techniques for making substitution mutations at predetermined sites in DNA having known sequence are well known, for example through M13 mutagenesis. The manipulation of DNA sequences to produce variant proteins which manifest as substitutional, insertional or deletional variants are well known in the art.

Other examples of recombinant or synthetic mutants and derivatives of the antibodies of the present invention include single or multiple substitutions, deletions and/or additions to any molecule associated with the ligand such as carbohydrates, lipids and/or proteins or polypeptides. Naturally occurring or altered glycosylated forms of the subject antibodies are particularly contemplated by the present invention.

Amino acid alterations to the subject polypeptide contemplated herein include insertions such as amino acid and/or carboxy terminal fusions as well as intra-sequence insertions of single or multiple amino acids. Generally, insertions within the amino acid sequence will be smaller than amino or carboxy terminal fusions, of the order of about 1 to 4 residues. Insertional amino acid sequence variants are those in which one or more amino acid residues are introduced into a predetermined site in the protein. Deletional variants are characterised by the removal of one or more amino acids from the sequence. Substitutional variants are those in which at least one residue in the sequence has been removed and a different residue inserted in its place. Such substitutions may be made in accordance with Table 1.

TABLE 1

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |

TABLE 1-continued

| Original Residue | Exemplary Substitutions |
| --- | --- |
| Gly | Val |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Pro | Ser; Ala |
| Ser | Thr |
| Thr | Ser |
| Trp | Tyr |
| Tyr | Trp; Phe |
| Val | Ile; Leu |

The terms "analogues" and "derivatives" also extend to any functional chemical equivalents of the antibodies characterised by their increased stability and/or efficacy in vivo or in vitro. The terms "analogue" and "derivatives" further extend to any amino acid derivative of the antibodies as described above.

Antibody analogues contemplated herein include, but are not limited to modifications to side chains, incorporation of unnatural amino acids and/or derivatising the molecules and the use of crosslinkers and other methods which impose conformational constraints on the antibodies. Examples of side chain modifications contemplated by the present invention include modifications of amino groups such as by reductive alkylation by reaction with an aldehyde followed by reduction with NaBH$_4$; amidination with methlacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbomoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) OR carbodiimide (COOH). In addition, peptides could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention, therefore, extends to amino acid and/or chemical analogues of the subject antibodies having the identifying characteristics of being interactive with the extracellular domain of the NYK/flk-1 receptor.

Accordingly, reference herein to an antibody includes the naturally occurring molecule, recombinant, synthetic and analogue forms thereof and to any mutants, derivatives and human and non-human homologues thereof including amino acid and glycosylation variants.

The immunointeractive molecules of the present invention may be used to develop a new range of therapeutic and diagnostic agents. For example, the antibodies or fragments or derivatives thereof may act as antagonists and be useful, for example, in the treatment of angiogenic-dependent phenotype and disease conditions resulting therefrom (e.g. metastasis). They may also be used for screening for agonists useful, for example, where angiogenesis is to be promoted. Normal or mutated receptor structure or receptor expression can also be determined through immunoreactivity studies.

According to this latter embodiment, there is contemplated a method of detecting a NYK/flk-1 receptor on a cell in a biological sample, said method comprising contacting said sample with an immunointeractive molecule capable of binding to the extracellular domain of said NYK/flk-1 receptor immobilised to a solid support for a time and under conditions sufficient for an immunointeractive molecule-NYK/flk1 complex to form and then detecting the presence of said complex.

In one preferred method, the immunointeractive molecule in NYK/flk-1 complex is detected by contacting the complex with an antibody against the immunointeractive molecule with the antibody being labelled with a reporter molecule. Alternatively, the immunointeractive molecule itself is labelled with a reporter molecule.

The immunointeractive molecules are generally antibodies and these, or antibodies directed against the immunointeractive molecules (e.g. anti-idotype antibodies), may be polyclonal or monoclonal antibodies. These are obtainable by immunisation of a suitable animal with the immunointeractive molecule (or NYK/flk-1 molecule), and either type is utilizable in the assay. The methods of obtaining both types of sera are well known in the art. Polyclonal sera are less preferred but are relatively easily prepared by injection of a suitable laboratory animal with an effective amount of immunointeractive molecule or NYK/flk-1 preparation, or antigenic parts thereof, collecting serum from the animal, and isolating specific antibodies by any of the known immunoadsorbent techniques. Although antibodies produced by this method are utilisable in virtually any type of assay, they are generally less favoured because of the potential heterogeneity of the product.

The use of monoclonal antibodies in the above immunoassay is particularly preferred because of the ability of produce them in large quantities and the homogeneity of the product. The preparation of hybridoma cell lines for monoclonal antibody production derived by fusing an immortal cell line and lymphocytes sensitised against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

The presence of a NYK/flk-1 receptor may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are particularly useful in the present invention. A number of variations of the sandwich assay technique exist, and all are intended to be encompassed by the present invention. Briefly, in one type of assay, an immunointeractive molecule is brought into contact with a biological sample comprising cells potentially carrying NYK/flk-1. After a suitable period of incubation, for a period of time sufficient to allow formation of an immunointeractive molecule-NYK/flk-1 complex, an antibody specific to the immunointeractive molecule, labelled with a reporter molecule capable of producing a detectable signal, is then added and incubated allowing sufficient time for the formation of a tertiary complex. Any unreacted material is washed away, and the presence of the antibody bound to the immunointeractive molecule is determined by observation of a signal produced by the reporter molecule. The results may either by qualitative, by simple observation of the visible signal, or may be quantitated by comparing with a control sample containing known amounts of antibody binding molecule. Variations on the forward assay include using an immunointeractive molecule labelled with a reporter molecule. In addition, the immunointeractive molecule or cells may be immobilised onto a solid support.

Suitable solid supports include glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consists of cross-linking, covalently binding or physically adsorbing the molecules to the polymer.

"Reporter molecule", as used in the present specification, is meant a molecule which, by its chemical nature, provides an analytically identifiable signal which allows the detection of antigen-bond antibody. Detection may be either qualitative or quantitative. The most commonly used reporter molecules in this type of assay are either enzymes, florophores or radionuclide containing molecules (i.e. radioisotopes) and chemiluminescent molecules.

In the case of an enzyme immunoassay, an enzyme is conjugated to the immunointeractive molecule or an antibody thereto generally by means of glutaraldehyde or periodate. As will be readily recognised, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chomogenic substrates noted above. Generally, the enzyme-labelled antibody is added to the immunointeractive molecule-receptor complex, allowed to bind, and then the excess reagent is washed away. Alternatively, an enzyme labelled immunointeractive molecule is used. A solution containing the appropriate substrate is then added to the tertiary complex. The substrate will react with the enzyme linked to the antibody/immunointeractive molecule, giving a qualitative visual signal, which may be further quantitated, usually spectrophotometrically, to give an indication of the amount of immunoreactive molecule which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. Immunofluorescence and EIA techniques are both very well established in the art and are particularly useful for the present method. However, other reporter molecules, such as radioisotope, chemiluminescent or bioluminescent molecules, may also be employed.

By detecting NYK/flk-1 receptors by the procedures, aberrant receptors may be discerned thus providing a useful screening procedure for potential disease conditions.

The present invention also provides a pharmaceutical composition comprising an effective amount of an immunointeractive molecule capable of binding or otherwise associating with the extracellular domain of NYK/flk-1 receptor and one or more pharmaceutically acceptable carriers and/or diluents. The active ingredients of a pharmaceutical composition comprising the immunointeractive molecules are contemplated to exhibit excellent therapeutic activity, for example, in the treatment of angiogenic-dependent phenotype and disease conditions resulting therefrom, such as metastasis, in an amount which depends on the particular case. For example, from about 0.5 $\mu$g to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredients which comprise the immunointeractive molecules may be required to be coated in a material to protect said ingredients from the action of enzymes, acids and other natural conditions which may inactivate said ingredients. In order to administer the immunointeractive molecules by other than parenteral administration, they will be coated by, or administered with, a material to prevent its inactivation. For example, the immunointeractive molecules may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylflurorphosphate (DEP) and trasylol. Liposomes include water-in-oil water emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monosterate and gelatin.

Sterile injectable solutions are prepared by incorporating the active compounds in the required amount in the appropriate solvent with various of the other ingredients enumerated above, as required, followed by filtered serialization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When immunointeractive molecules are suitably protected as described above, the active, compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.5 $\mu$g and 2000 mg of active compound.

The tablets, troches, pills, capsules and the like may also contain the following: A binder such as gum tragacanth, acacia, corn starch, potato starch, alginic acid and the like; a lubricant such as magnesium stearate; and a sweetening agent such a sucrose, lactose and saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 μg to about 2000 mg. Expressed in proportions, the active compound is generally present in from about 0.5 μg to about 2000 mg/ml of carrier. In the case of compositions containing supplementary active ingredients, the dosages are determined by reference to the usual dose and manner of administration of the said ingredients.

In a most preferred embodiment, the immunointeractive molecules used in a pharmaceutical composition are antibodies or mutants or derivatives thereof. Most preferably, the antibodies are monoclonal antibodies.

The present invention is further described by reference to the following non-limiting examples.

EXAMPLE 1

Cell Culture

The mouse myeloma P3X63Ag8.653(NS-1) was maintained in Dulbecco's modified Eagle's medium supplemented with 10% v/v HI-FBS, 5 mM L-glutamine, 50 μg/ml gentamycin, grown at 37° C. in a humidified atmosphere of 10% v/v $CO_2$. Hybridomas were grown in supplemented DMEM plus 10 μg/ml of recombinant IL-6 (rIL-6) at all stages after removal from the hypoxanthine/aminopterin/thymidine (HAT) selection medium. NIH-3T3 cells transfected with the AP-TAG-1 constructs were selected in supplemented DMEM containing 700 μg/ml G418. CHO cell lines were grown in Glasgow Minimal Essential Medium supplemented with 50 μg/ml gentamycin, non-essential amino acids, sodium pyruvate, glutamate and asparagine, nucleosides and 25 mM methionine sulphoxide (MSX). COS cells were maintained in RPMI-1640 medium with supplements at 37° C. and 5% v/v $CO_2$ and transfected using the DEAE-dextran protocol (8).

EXAMPLE 2

Construction of Truncated Forms of the NYK Receptor

To obtain constructs which would encode various portions of the NYK extracellular domain, site-directed mutagenesis was employed to generate specific inframe restriction enzyme sites within the clone.

The full length clone of the NYK/flk-1 receptor described by Oelrichs et al (2) was subcloned into the mammalian expression vector μ cDNA1-amp (Invitrogen, San Diego, Calif.) using the BstXI restriction enzyme site. Single stranded DNA was generated using the M13 origin of replication, and this DNA used as a template to make NYK cDNA containing specific enzyme sites. Inframe BglII sites were introduced after the final beta strand of a given Ig-like domain to produce contructs which could then be ligated into the (5')HindIII-(3')BglII site of the expression vector AP-TAG-1. BglII sites were introduced to produce constructs containing the two most N-terminal domains (D1-D2), the first three domains (D1-D2-D3), the first five domains (D1-D2-D3-D4-D5) or the entire extracellular domain (NYK-EX-D1-D7-AP). HindIII-BglII fragments of these mutants were then ligated into the HindIII-BglII site of AP-TAG-1 to produce D1-D2-AP, D1-D2-D3-AP, D1-D5-AP, D1-D7-AP. The resultant plasmids were co-transfected with pgk-neo into NIH-3T3 fibroblasts and selected by their ability to grow in 700 μg/ml G418. Linese secreting the AP fusion proteins were selected using the conversion of the substrate PNPP (Southern Biotechnology Associates) which detects AP activity in the tissue culture supernatants (9). Endogenous AP activity is reduced by heating the samples at 65° C. for 10 minutes prior to assaying.

The mutant NYK receptor containing the BglII site located at the junction of the extracellular domain and the transmembrane domain (NYK-EX-BglII) was used to ligate a oligonucleotide linker sequence encoding the FLAG™ marker peptide (IBI), and in frame stop codon, BglII compatible ends and an internal ClaI site. (IBI; 5'-GATCTGACTACAAGGACGACGACGATGACAAG-TGAATCGATA-3' [SEQ ID NO:2], (N)Asp-Tyr-Lys-Asp-Asp-Asp-Lys-Term(C) [SEQ ID NO:1]). The entire NYK cDNA was then transferred (5' XbaI-3' XbaI) into the XbaI site of the CHO cell expression vector. This construct was transfected into CHO-K1 cells and positive clones selected in medium containing 25 mM (MSX). Expressing clones were selected by immunoprecipitation of $^{35}S$-methionine labelled cells with anti-FLAG™ (M2) antibody gel.

A cDNA clone encoding the MW 165 amino acid form of VEGF was isolated using the polymerase chain technique from mouse lung cDNA library (6 week female C57BL CBA) [Stratagene, Cat #936307] in lambda 2APII vector. The fragment was subcloned into the vector pCDM8 and used for transient expression in COS cells. Supernatents from these cells demonstrated vascular permeability in the Miles assay indicating that the clone was indeed functional. This fragment was removed by XbaI digest and subcloned into a CHO cell expression vector.

COS cells were transiently transfected using the DEAE Dextran method as previously described. Supernatant's were assayed on days 5 to 7 following transfection to determine VEGF activity.

EXAMPLE 3

Affinity Chromatography

NYK-D1-D7FLAG™ was purified from the expended tissue culture supernatant of NYK-D1-D7-FLAG™-CHO by affinity chromatography on a M2 (anti-FLAG™) gel (IBI). Supernatant (100 ml) was passed over the M2 column then subsequently washed with 10 mM Tris-HCl pH 8.0, 150 mM NaCl, 0.02 v/v Tween 20; 50 mM TEA pH 10.0, 150 mM NaCl, 0.02% v/v Tween 20 (optional) and again with 10 mM Tris-HCl pH 8.0, 150 mM NaCl, 0.02% v/v Tween 20. Bound material was eluted with either 100 mM glycine-HCl pH 3.0 (neutralised in 1/10 volume 1M Tris-HCl pH 8.6) or 25 μg/ml FLAG™ peptide (N-Asp-Tyr-Lys-Asp-Asp-Asp-Asp-Lys-C [SEQ ID NO: 1]) in 10 mM Tris-HCl pH 8.0, 150 mM NaCl, 0.02% v/v Tween 20. Both of these elution techniques gave about 90–95% pure NYK-D1-D7-FLAG™ by SDS PAGE. For immunisations and coupling to the sensor chip these proteins were further purified by ion-exchange chromatography (MonoQ, HPLC 1090) to give a single homogenous species corresponding to NYK-FLAG™.

HPLC purified NYK-FLAG™ (1 mg) was coupled to Affi-Gel 10 beads using NHS chemistry. This affinity column was then used to isolate VEGF from CHO cell supernatants.

EXAMPLE 4

Monoclonal Antibody Production

Purified NYK-D1-D7-FLAG™ (approx 10 μg) was used to immunise female Wistar rats on day 52 (i.p.), 28 (i.p.) and 3 (i.v. and i.p.) prior to fusion with the mouse myeloma P3X63Ag8.653 (NS-1). NYK-D1-D7-FLAG™ was prepared for the first two i.p. immunisations by combining with adjuvant containing trehalose dimycolate from *Mycobacterium phlei*, monophosphoryl lipid A from *Salmonella minnesota* R595, PBS/0.2% v/v Tween 80 and squalene as described in the manufacturers instructions (RIBI Immunochem Research, Hamilton, Mont.). The final immunisation was performed with purified NYK-D1-D7-FLAG™ diluted 1/1 with PBS. Rats were test bled on day 18 prior to fusion and the titre of anti-NYK-D1-D7-FLAG™ antibodies determined by a solid phase EIA and immunoprecipitation of NYK-D1-D7-FLAG™.

Monoclonal antibodies to the NYK extracellular domain were selected by screening the fusion on purified NYK-D1-D7FLAG™ and tie2 extracellular domain-FLAG™ by an enzyme immunoassay. Briefly, 96 well PVC microtitre plates were coated with either NYK-D1-D7-FLAG™ or tie2-EX-FLAG™ at a level previously determined by reactivity with an anti-FLAG™ antibody (M2) to give an equivalent signal. Hybridoma supernatants were added and incubated for 2 h at 4° C. followed by six washes with PBS/0.02% v/v Tween 20 (buffer). Incubation with a horse raddish peroxidase conjugated rabbit anti-Rat Ig followed for 1 h at 4° C. After washing, the assay was developed with an ABTS substrate system and the assay quantitated by reading absorbances at 405 nm in a multiwell plate reader (Flow Laboratories MCC/340, McLean, Va.). Antibodies selected for further analysis were subcloned twice by limiting dilution. These antibodies were designated 4H3, 3B6, 3C8.

EXAMPLE 5

Purification of Rat Monoclonal Antibodies

Rat monoclonal antibodies were purified using the technique of Darby et al., (10). Briefly, FCS was depleted of bovine IgG by serial passage over a protein G Sepharose fast flow gel. The resulting bovine IgG depleted serum was used for the bulk culture of the rat hybridoma cell line. Cells were grown in roller bottles containing DMEM, 10% v/v IgG depleted FCS, 5 mM L-glutamine, 50 µg/ml gentamicin and 10 µg/ml recombinant IL-6 until expiration and the supernatant removed from the cellular debris. Rat IgG was subsequently purified by affinity chromatography on protein G-Sepharose and the yield assessed by $OD_{280}$.

Antibodies were dialysed versus PBS for use in assays. For coupling to CNBr-activated Sepharose beads (Pharmacia) the antibodies were dialysed aganist 0.1M $NaHCO_3$/0.5M NaCl and then conjugated at about 2 mg of antibody per ml of beads. Protein A purified rabbit Ig was also coupled to the Sepharose beads as a non-binding control.

EXAMPLE 6

Cell Labellings and Immunoprecipitations

Subconfluent monolayers of either NIH-3T3 fibroblasts or CHO-K1 cells transfected with the various NYK domain constructs were starved in Met Cys medium containing 5% v/v FCS, 5 mM L-glutamine and 50 µg/ml gentamycin for 0.5 h prior to incubating with 100 µCi $^{35}$[S] cysteine/methionine (Translabel, ICN) per $10^6$ cells. After a 16 h incubation at 37° C. supernatants were collected and used for immunoprecipitation analysis. Supernatants were incubated with 10 µl to anti-FLAG™ M2 affinity gel or 10 µl of 4H3-Sepharose or 3B6Sepharose at 4° C. with rotation for 2–4 h. Immunoprecipitates were washed three times with 10 mM Tris-HCl pH 8.0, 150 mM NaCl, 1% v/v Triton X-100 and then twice with 10 mM Tris-HCl pH 8.0, 150 mM NaCl, 0.1% v/v Triton X-100 then 10 mM Tris-HCl pH 8.0. Immunoprecipitates were boiled in 2×SDS PAGE sample buffer and analysed by denaturing polyacrylamide gel electrophoresis.

EXAMPLE 7

Biosensor Experiments

Binding studies and Epitope mapping were preformed on the optical biosensor (BIAcore™, Pharmacia, Uppsala) using proteins immobilised to a CM5 sensor chip. Immobilisation of NYK-FLAG™, VEGF and monoclonal antibodies were performed using standard NHS chemistry and using conditions recommended by the manufacturers instructions. Integrity of immobilised protein was examined with the appropriate ligand prior to commencement of an experiment.

EXAMPLE 8

To develop antibodies specifically directed to the extracellular domain of the NYK receptor, a construct was produced containing the NYK extracellular domain fused in frame to the FLAG™ marker peptide. This was achieved by introducing a BgIII site at the junction of the extracellular domain and the transmembrane domain of the receptor by site-directed mutagenesis. An oligonucleotide linker sequence encoding the FLAG™ marker peptide, an in frame stop codon and having BgIII cut ends was then ligated into this site and successfully ligated plasmids selected by a ClaI site within the liker sequence. Expression analysis in COS cells demonstrated a protein of the expected size which could be specifically immunoprecipitated by the M2 (anti-FLAG™) gel. The construct was subcloned into the CHO cell expression vector pEE6 for large scale production of the NYK-EX-FLAG™ protein.

The NYK-EX-FLAG™ protein was purified from CHO cell supernatants by affinity chromatography on M2 antibody gel and elution with the free FLAG™ peptide. Subsequent purification by ion-exchange chromatography removed the free peptide and other contaminants giving a single homogenous species of $M_w$, 120,000–130,000 by SDS PAGE which is consistent with the predicted size of the extracellular domain plus glycosylation. Rats were immunised with the NYK-EX-FLAG™ protein and upon achieving an appropriate response their spleen cells were fused with the mouse myeloma NS-1 using standard somatic cell hybridisation techniques. Antibodies were selected on the basis of their reactivity to purified NYK-EX-FLAG™ compared to another fusion protein containing the extracellular domain of the tie2 receptor ligated to the FLAG™ marker peptide. To determine if these antibodies could recognise the NYK extracellular domain, cell lines expressing the NYK-EX-FLAG™ and NYK-EX-AP were biosynthetically labelled with $^{35}$S Cys-Met and used for immunoprecipitation experiments. Three monoclonal antibodies were shown to specifically immunoprecipitate the NYK-EX-FLAG™ and NYK-D1-D7AP protein indicating they recognise the native NYK extracellular domain. The antibodies have also been shown to react with the NYK-EX-FLAG™ coupled to the optical biosensor; NYK on the biosensor chip is active in that it binds the 165 amino acid form of VEGF from CHO cell supernatants. Characterisation of two of the monoclonal antibodies on domain mutants of the NYK extracellular region show that 4H3 and 3B6 immunoprecipitate the D1-D2AP, D1-D2-D3-AP, D1-D5-AP and D1-D7-AP fusion proteins indicating that their binding sites are restricted to the two most N-terminal Ig-like domains.

EXAMPLE 9

Recent studies by Pacific and Thompson (1994) suggest that most RTKs when transfected into factor-dependent cell lines such as FDCP-1 and BA/F3 do not produce a significant proliferative response to ligand. However, if a chimeric molecule comprising the extracellular domain of the RTK and the transmembrane and cytoplasmic domain of the cytokine receptor for erythropoietin (EpoR) is used, the level of proliferation achieved is similar to that given by the wildtype cytokine responses to be generated.

Using site directed mutagenesis a silent mutation in the EpoR cytoplasmic domain was effected to remove a BgIII restriction enzyme site as position 866 of the mouse Epo receptor published nucleotide sequence (D'Andrea et al, 1989). Another BgIII siege was then subsequently introduced at the junction of the extracellular domain and putative transmembrane domain of the EpoR. The cytoplasmic and transmembrane domain of the EpO receptor was then ligated in frame to the extracellular domain of the NYK receptor via the BgIII site. The insert was then subcloned into the pBOS expression vector via XbaI. This construct is designated pBOS-NYK-Epo.

pBOS-NYK-EpoR was then cotransfected into the factor-dependent pre-B cell line Ba/F3 with the neomycin resistance plasmid. The BA/F3 cell lines is dependent on the presence of IL-3/GM-CSF for growth; removal of these factors results in rapid cell death with 24–48 h. Cells were selected in DMEM, 10% HI FCS, 50 µg/ml gentamycin, 5 mM L-glutamine and 1.2 mg/ml G418 growth medium. Individual clones growing after 7–14 days were picked and expanded in liquid culture.

NYK-EpoR expressing colonies were selected by two procedures:
  (i) immunoprecipitation of $^{35}$S-met/Cys/labelled receptors with anti-NYK mAbs and analysis by SDS-PAGE;
  (ii) stimulation of the cell line with ligand (VEGF).

1000 NYK-EpoR-BA/F3 cells or non-expressing control BA/F3 cells were resuspended in a 15 µl volume of growth medium containing 10% medium conditioned by the growth of COS cells transfected with pCDM8-VEGF$_{165}$ or dilutions of antibody. Stimulation of cells was judged over a period of 2–14 days when compared to control populations.

Three cell lines were demonstrated to respond to VEGF and to express the NYK-EpoR chimera, as summarised in Table 2. These cell lines were also shown to be specifically stimulated to grow by incubation with 10–20 µg/ml of mAbs directed to the extracellular domain of the NYK receptor (see Table 3). This is presumed to be the result of cross-linking of receptors at the cell surface, which mimics ligand-induced dimerisation of the receptor.

The assay therefore specifically detects interactions of the NYK extracellular domain and its ligand VEGF, and is therefore useful for detection and evaluation of substances that may modulate this interaction, or detection and evaluation of inhibitors of such modulatory substances.

Transfected or untransfected BA/F3 cells were removed from WEHI3D conditioned medium, washed twice in PBS and resuspended in medium containing 5 ng/ml of VEGF$_{165}$.

Growth was determined after 10 days exposure of VEGF by visual inspection of cultures.

TABLE 2

Stimulation of NYK-EpoR Transfected BA/F3 Cells

| Clone | WEHI3D conditioned medium | VEGF165 | Growth |
|---|---|---|---|
| BA/F3 | + | − | +++ |
| BA/F3 | − | + | − |
| BA/F3 vector only | − | + | − |
| BA/F3-NYK-Epo#2 | − | + | ++ |
| BA/F3-NYK-EPoR#18 | − | + | ++ |
| BA/F3-NYK-EpoR#23 | − | + | ++ |

TABLE 3

Stimulation of NYK-EpoR Transfected BA/F3 Cells with Monoclonal Antibodies to the NYK Receptor Extracellular Domain

| Clone | WEHI3D | Anti-NYK Mab | Growth |
|---|---|---|---|
| BA/F3 | + | − | +++ |
| BA/F3 | − | + | − |
| BA/F3 Vector Only | − | + | − |
| BA/F3-NYK-EpoR#23 | − | + | ++ |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually, or collectively, and any and all combinations of any two or more of said steps or features.

REFERENCES

1. Folkman, J., Shing, Y. *J. Biol. Chem.* 267: 10931, 1992.
2. Oelrichs, R. B., Reid, H. H., Bernard, O., Ziemiecki, A., Wilks, A. F. *Oncogene* 8: 11, 1993.
3. Runting, A. S. Stacker, S. A., Wilks, A. F., *Growth Factors* 9: 99, 1993.
4. Terman, B. I., Dogher-Vermazen, M., Carrion, M. E., Dimitrov, D., Armellino, D. C., Gospodarowicz, D., Bohlen, P. *Biochem. Biophys. Res. Commun.* 187: 1579, 1993.
5. Keck, P. J., Hauser, S. D., Krivi, G., Sanzo, K., Warren, T., Feder, J., Connolly, D. T. *Science* 246: 1309, 1989.
6. Plate, K. H., Brier, G., Weich, H. A., Risau, W. *Nature* 359: 845, 1993.
7. Kim, K. J., Li, B., Winer, J., Armanini, M., Gillett, N., Phillips, H. S., Ferrara, N. *Nature* 362: 841, 1993.
8. Aruffo, A., Seed, B. *Proc. Natl. Acad. Sci. USA* 84: 8573, 1987.
9. Flanagan, J. G., Leder, P. *Cell* 63: 185, 1990.
10. Darby, C. R., Hamano, K., Wood, K. J., *J. Immunol. Methods* 159: 125, 1993.

What is claimed is:

1. A monoclonal antibody that binds to an extracellular domain of a mammalian growth factor receptor protein neuroepithelial kinase/fetal liver kinase, NYK/flk-1, wherein said monoclonal antibody binds to said extracellular domain at a point defined by the first two Ig domains of said NYK/flk-1.

2. The monoclonal antibody of claim 1 wherein the mammalian growth factor receptor is from a human, livestock animal, laboratory test animal, companion animal or captive wild animal.

3. The monoclonal antibody of claim 2 wherein the mammalian growth factor receptor is from a human or a murine animal.

4. The monoclonal antibody of claim 1 wherein the neuroepithelial kinase/fetal liver kinase NYK/flk-1 receptor extracellular domain is fused to a carrier molecule.

5. The monoclonal antibody of claim 4 wherein the carrier molecule is FLAG™ peptide.

6. The monoclonal antibody of claim 4 wherein the carrier molecule is alkaline phosphatase.

7. The monoclonal antibody of claim 3, wherein said mammalian growth factor is from a human.

* * * * *

UNITED STATES PATENT AND TRADEMARK OFFICE
CERTIFICATE OF CORRECTION

PATENT NO. : 6,218,516 B1
DATED : April 17, 2001
INVENTOR(S) : Wilks, et al.

Page 1 of 1

It is certified that error appears in the above-identified patent and that said Letters Patent is hereby corrected as shown below:

Title page,
References, U.S. Pantent Docs change "9" to -- 14 --.

Column 1,
Line 33, change "tyrosien" to -- tyrosine --.
Line 47, change "meadiating" to -- mediating --.

Column 7,
Line 9, change "of" second occorence to -- to --.

Column 12,
Line 8, change "and" to -- an --.

Title page,
Assignee delete "London (GB)" and insert -- New York, NY --.

Signed and Sealed this

Eleventh Day of September, 2001

*Attest:*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO. : 6,218,516 B1
DATED : April 17, 2001
INVENTOR(S) : Wilks et al.

It is certified that error appears in the above-identified patent and that said Letters Patent is hereby corrected as shown below:

Title page,
Item [73], Assignee, delete "London (GB)" and insert -- New York, NY --.
Item [56], OTHER PUBLICATIONS, change "9" to -- 14 --.

Column 1,
Line 33, change "tyrosien" to -- tyrosine --.
Line 47, change "meadiating" to -- mediating --.

Column 7,
Line 9, change "of" to -- to --.

Column 12,
Line 8, change "and" to -- an --.

Signed and Sealed this

Seventh Day of January, 2003

JAMES E. ROGAN
*Director of the United States Patent and Trademark Office*

SEQUENCE LISTING

<160> NUMBER OF SEQ ID NOS: 3

<210> SEQ ID NO 1
<211> LENGTH: 8
<212> TYPE: PRT
<213> ORGANISM: Mus musculus

<400> SEQUENCE: 1

Asp Tyr Lys Asp Asp Asp Asp Lys
1               5

<210> SEQ ID NO 2
<211> LENGTH: 39
<212> TYPE: DNA
<213> ORGANISM: Mus musculus

<400> SEQUENCE: 2
gatctgacta caaggacgac gatgacaagt gaatcgata                              39

<210> SEQ ID NO 3
<211> LENGTH: 39
<212> TYPE: DNA
<213> ORGANISM: Mus musculus

<400> SEQUENCE: 3
gatctatcga ttcacttgtc atcgtcgtcc ttgtagtca                              39